US011944558B2

(12) United States Patent
Deen et al.

(10) Patent No.: US 11,944,558 B2
(45) Date of Patent: Apr. 2, 2024

(54) MEDICAL DEVICE DELIVERY DEVICES, SYSTEMS, AND METHODS

(71) Applicant: Covidien LP, Mansfield, MA (US)

(72) Inventors: Daniel Deen, Long Beach, CA (US); Ashok Nageswaran, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 311 days.

(21) Appl. No.: 17/444,502

(22) Filed: Aug. 5, 2021

(65) Prior Publication Data

US 2023/0038177 A1  Feb. 9, 2023

(51) Int. Cl.
*A61F 2/82* (2013.01)
*A61F 2/90* (2013.01)
(Continued)

(52) U.S. Cl.
CPC .................. *A61F 2/95* (2013.01); *A61F 2/90* (2013.01); *A61F 2002/823* (2013.01); *A61F 2002/9505* (2013.01)

(58) Field of Classification Search
CPC .......... A61F 2/95; A61F 2/011; A61F 2/2427; A61F 2/243; A61F 2/2433; A61F 2/2436; A61F 2/966; A61F 2002/9505; A61F 2002/9511; A61B 2017/1205; A61B 2017/12054; A61M 39/10;
(Continued)

(56) References Cited

U.S. PATENT DOCUMENTS 3,416,531 A    12/1968  Lowell
4,364,391 A    12/1982  Toye
(Continued)

FOREIGN PATENT DOCUMENTS

CN    104582643 A    4/2015
CN    105232195 A    1/2016
(Continued)

OTHER PUBLICATIONS

International Search Report and Written Opinion dated May 23, 2022, International Application No. PCT/US2022/012747, 15 pages.
(Continued)

*Primary Examiner* — Kelly J Bekker
*Assistant Examiner* — Lindsey R. Rivers
(74) *Attorney, Agent, or Firm* — Fortem IP LLP; Matt Lincicum

(57) ABSTRACT

A medical device delivery system includes a joining element with a bumper having a distal end portion configured to engage a proximal portion of a medical device and a proximal end portion adjacent a distal end portion of an elongated tubular member. The proximal end portion defines a slot having a length along a first direction. The joining element further includes an aperture extending through the bumper and having a first, greater, cross-sectional dimension along a second direction and a second, smaller, cross-sectional dimension along a third direction. The system can include an elongated shaft having a distal region and a flattened region proximal of the distal region, the flattened region having a greatest cross-sectional dimension that is smaller than the first cross-sectional dimension but larger than the second cross-sectional dimension The flattened region can be received within the slot.

19 Claims, 12 Drawing Sheets

(51) Int. Cl.
  *A61F 2/95* (2013.01)
  *A61F 2/966* (2013.01)

(58) Field of Classification Search
  CPC .......... A61M 39/1011; A61M 39/1055; A61M 2039/1027; A61M 2039/1033; A61M 2039/1077; A61M 25/0032; A61M 25/0097; A61M 2025/0063; A61M 2025/0098
  See application file for complete search history.

(56) References Cited

U.S. PATENT DOCUMENTS

| | | |
|---|---|---|
| 4,425,919 A | 1/1984 | Alston et al. |
| 4,516,972 A | 5/1985 | Samson |
| 4,723,936 A | 2/1988 | Buchbinder et al. |
| 4,877,031 A | 10/1989 | Conway et al. |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,037,427 A | 8/1991 | Harada et al. |
| 5,061,275 A | 10/1991 | Wallsten et al. |
| 5,098,393 A | 3/1992 | Amplatz et al. |
| 5,108,411 A | 4/1992 | McKenzie |
| 5,147,370 A | 9/1992 | McNamara et al. |
| 5,178,158 A | 1/1993 | De |
| 5,201,316 A | 4/1993 | Pomeranz et al. |
| 5,209,734 A | 5/1993 | Hurley et al. |
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,525 A | 6/1994 | West et al. |
| 5,318,529 A | 6/1994 | Kontos |
| 5,358,493 A | 10/1994 | Schweich et al. |
| 5,382,259 A | 1/1995 | Phelps et al. |
| 5,389,087 A | 2/1995 | Miraki |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St et al. |
| 5,545,209 A | 8/1996 | Roberts et al. |
| 5,554,139 A | 9/1996 | Okajima |
| 5,569,220 A | 10/1996 | Webster |
| 5,571,135 A | 11/1996 | Fraser et al. |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso |
| 5,636,641 A | 6/1997 | Fariabi |
| 5,645,559 A | 7/1997 | Hachtman et al. |
| 5,658,264 A | 8/1997 | Samson |
| 5,662,622 A | 9/1997 | Gore et al. |
| 5,676,659 A | 10/1997 | McGurk |
| 5,695,483 A | 12/1997 | Samson |
| 5,695,499 A | 12/1997 | Helgerson et al. |
| 5,702,373 A | 12/1997 | Samson |
| 5,702,418 A | 12/1997 | Ravenscroft |
| 5,704,926 A | 1/1998 | Sutton |
| 5,709,703 A | 1/1998 | Lukic et al. |
| 5,711,909 A | 1/1998 | Gore et al. |
| 5,716,410 A | 2/1998 | Wang et al. |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio et al. |
| 5,743,876 A | 4/1998 | Swanson |
| 5,755,777 A | 5/1998 | Chuter |
| 5,759,173 A | 6/1998 | Preissman et al. |
| 5,776,141 A | 7/1998 | Klein et al. |
| 5,782,811 A | 7/1998 | Samson et al. |
| 5,791,036 A | 8/1998 | Goodin et al. |
| 5,824,041 A | 10/1998 | Lenker et al. |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | Van |
| 5,853,400 A | 12/1998 | Samson |
| 5,873,866 A | 2/1999 | Kondo et al. |
| 5,876,386 A | 3/1999 | Samson |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,968,069 A | 10/1999 | Dusbabek et al. |
| 5,971,975 A | 10/1999 | Mills et al. |
| 5,984,963 A | 11/1999 | Ryan et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,077,297 A | 6/2000 | Robinson et al. |
| 6,083,152 A | 7/2000 | Strong |
| 6,093,177 A | 7/2000 | Javier et al. |
| 6,105,651 A | 8/2000 | Leanna |
| 6,106,510 A | 8/2000 | Lunn et al. |
| 6,106,540 A | 8/2000 | Dehdashtian et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,389,087 B1 | 5/2002 | Heinonen et al. |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |

(56) References Cited

U.S. PATENT DOCUMENTS

| | | |
|---|---|---|
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |
| 6,468,298 B1 | 10/2002 | Pelton |
| 6,475,184 B1 | 11/2002 | Wang et al. |
| 6,494,907 B1 | 12/2002 | Bulver |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Soenderskov |
| 6,602,271 B2 | 8/2003 | Adams et al. |
| 6,607,551 B1 | 8/2003 | Sullivan et al. |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |
| 6,648,654 B1 | 11/2003 | Hembree |
| 6,648,874 B2 | 11/2003 | Parisi et al. |
| 6,652,508 B2 | 11/2003 | Griffin et al. |
| 6,663,614 B1 | 12/2003 | Carter |
| 6,669,719 B2 | 12/2003 | Wallace et al. |
| 6,689,120 B1 | 2/2004 | Gerdts |
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 | 7/2004 | Wang et al. |
| 6,808,529 B2 | 10/2004 | Fulkerson |
| 6,814,749 B2 | 11/2004 | Cox et al. |
| 6,815,325 B2 | 11/2004 | Ishii |
| 6,817,995 B1 | 11/2004 | Halpern |
| 6,830,575 B2 | 12/2004 | Stenzel et al. |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,866,660 B2 | 3/2005 | Garabedian et al. |
| 6,866,679 B2 | 3/2005 | Kusleika |
| 6,932,837 B2 | 8/2005 | Amplatz et al. |
| 6,939,353 B2 | 9/2005 | Que et al. |
| 6,945,970 B2 | 9/2005 | Pepin |
| 6,960,227 B2 | 11/2005 | Jones et al. |
| 6,984,963 B2 | 1/2006 | Pidutti et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,156,860 B2 | 1/2007 | Wallsten |
| 7,163,523 B2 | 1/2007 | Devens et al. |
| 7,166,088 B2 | 1/2007 | Heuser |
| 7,166,099 B2 | 1/2007 | Devens |
| 7,166,100 B2 | 1/2007 | Jordan et al. |
| 7,172,575 B2 | 2/2007 | El-Nounou et al. |
| 7,223,263 B1 | 5/2007 | Seno |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,404,820 B2 | 7/2008 | Mazzocchi et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens |
| 7,507,229 B2 | 3/2009 | Hewitt et al. |
| 7,524,322 B2 | 4/2009 | Monstadt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | McFerran et al. |
| 7,641,646 B2 | 1/2010 | Kennedy |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,740,652 B2 | 6/2010 | Gerdts et al. |
| 7,758,624 B2 | 7/2010 | Dorn et al. |
| 7,766,820 B2 | 8/2010 | Core |
| 7,766,896 B2 | 8/2010 | Kornkven et al. |
| 7,780,646 B2 | 8/2010 | Farnholtz |
| 7,815,600 B2 | 10/2010 | Al-Marashi et al. |
| 7,815,608 B2 | 10/2010 | Schafersman et al. |
| 7,815,628 B2 | 10/2010 | Devens |
| 7,828,790 B2 | 11/2010 | Griffin |
| 7,867,267 B2 | 1/2011 | Sullivan et al. |
| 7,879,022 B2 | 2/2011 | Bonnette et al. |
| 7,935,140 B2 | 5/2011 | Griffin |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstadt et al. |
| 8,066,754 B2 | 11/2011 | Malewicz |
| 8,083,791 B2 | 12/2011 | Kaplan et al. |
| 8,088,140 B2 | 1/2012 | Ferrera et al. |
| 8,092,508 B2 | 1/2012 | Leynov et al. |
| 8,109,987 B2 | 2/2012 | Kaplan et al. |
| 8,133,266 B2 | 3/2012 | Thomas et al. |
| 8,147,534 B2 | 4/2012 | Berez et al. |
| 8,187,314 B2 | 5/2012 | Davis et al. |
| 8,257,432 B2 | 9/2012 | Kaplan et al. |
| 8,298,276 B2 | 10/2012 | Ozawa et al. |
| 8,317,850 B2 | 11/2012 | Kusleika |
| 8,337,543 B2 | 12/2012 | Jordan et al. |
| 8,366,763 B2 | 2/2013 | Davis et al. |
| 8,382,818 B2 | 2/2013 | Davis et al. |
| 8,480,701 B2 | 7/2013 | Monstadt |
| 8,579,958 B2 | 11/2013 | Kusleika |
| 8,591,566 B2 | 11/2013 | Newell et al. |
| 8,597,321 B2 | 12/2013 | Monstadt et al. |
| 8,636,760 B2 | 1/2014 | Garcia et al. |
| 8,679,172 B2 | 3/2014 | Dorn et al. |
| 8,790,387 B2 | 7/2014 | Nguyen et al. |
| 8,858,613 B2 | 10/2014 | Cragg et al. |
| 8,968,383 B1 | 3/2015 | Johnson et al. |
| 9,393,141 B2 | 7/2016 | Gerdts et al. |
| 9,439,795 B2 | 9/2016 | Wang et al. |
| 9,474,639 B2 | 10/2016 | Haggstrom et al. |
| 9,775,733 B2 | 10/2017 | Johnson et al. |
| 9,782,186 B2 | 10/2017 | Johnson et al. |
| 9,827,126 B2 | 11/2017 | Losordo et al. |
| 10,786,377 B2 | 9/2020 | Nageswaran et al. |
| 10,945,867 B2 | 3/2021 | Nageswaran et al. |
| 11,071,637 B2 | 7/2021 | Dawson et al. |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |
| 2002/0029046 A1 | 3/2002 | Lorentzen et al. |
| 2002/0045929 A1 | 4/2002 | Diaz |
| 2002/0049412 A1 | 4/2002 | Madrid et al. |

(56) References Cited

U.S. PATENT DOCUMENTS

| | | |
|---|---|---|
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2002/0188342 A1 | 12/2002 | Rykhus et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092868 A1 | 5/2004 | Murray |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0204749 A1 | 10/2004 | Gunderson |
| 2004/0220585 A1 | 11/2004 | Nikolchev et al. |
| 2004/0230285 A1 | 11/2004 | Gifford et al. |
| 2004/0260271 A1 | 12/2004 | Huyser et al. |
| 2004/0260384 A1 | 12/2004 | Allen |
| 2004/0267348 A1 | 12/2004 | Gunderson et al. |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | McFerran |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0267563 A1* | 12/2005 | Case ........................ A61F 2/958 623/1.11 |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | McFerran et al. |
| 2006/0095050 A1 | 5/2006 | Hartley et al. |
| 2006/0100687 A1 | 5/2006 | Fahey et al. |
| 2006/0100688 A1 | 5/2006 | Jordan et al. |
| 2006/0116750 A1 | 6/2006 | Hebert et al. |
| 2006/0129166 A1 | 6/2006 | Lavelle |
| 2006/0178698 A1 | 8/2006 | McIntyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2006/0271093 A1 | 11/2006 | Holman et al. |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0149927 A1 | 6/2007 | Itou et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee |
| 2008/0132933 A1 | 6/2008 | Gerber |
| 2008/0132989 A1 | 6/2008 | Snow et al. |
| 2008/0140180 A1 | 6/2008 | Dolan et al. |
| 2008/0147001 A1 | 6/2008 | Al-Marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |

(56) References Cited

U.S. PATENT DOCUMENTS

| | | |
|---|---|---|
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0137403 A1 | 6/2011 | Rasmussen et al. |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | McHugo et al. |
| 2011/0208292 A1 | 8/2011 | Von et al. |
| 2011/0224650 A1 | 9/2011 | Itou et al. |
| 2011/0257720 A1 | 10/2011 | Peterson et al. |
| 2011/0288626 A1 | 11/2011 | Straubinger et al. |
| 2011/0319904 A1 | 12/2011 | Hollett et al. |
| 2012/0029607 A1 | 2/2012 | McHugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0226343 A1 | 9/2012 | Vo et al. |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274855 A1 | 10/2013 | Stante et al. |
| 2013/0274859 A1 | 10/2013 | Argentine |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulos et al. |
| 2014/0172067 A1 | 6/2014 | Brown et al. |
| 2014/0194919 A1 | 7/2014 | Losordo et al. |
| 2014/0200648 A1 | 7/2014 | Newell et al. |
| 2014/0276541 A1* | 9/2014 | Ahluwalia ...... A61M 25/10184 604/97.02 |
| 2014/0277332 A1 | 9/2014 | Slazas et al. |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0133990 A1 | 5/2015 | Davidson |
| 2015/0164666 A1 | 6/2015 | Johnson et al. |
| 2015/0238336 A1 | 8/2015 | Johnson et al. |
| 2016/0113793 A1 | 4/2016 | Nishigishi |
| 2016/0206454 A1 | 7/2016 | Fischell et al. |
| 2017/0035592 A1 | 2/2017 | Haggstrom et al. |
| 2017/0252161 A1 | 9/2017 | Tran et al. |
| 2018/0042745 A1 | 2/2018 | Losordo et al. |
| 2018/0200092 A1 | 7/2018 | Nageswaran et al. |
| 2018/0263799 A1 | 9/2018 | Elwood et al. |
| 2018/0311061 A1 | 11/2018 | Nolan et al. |
| 2019/0151124 A1 | 5/2019 | Hammersmark et al. |
| 2019/0314175 A1 | 10/2019 | Dawson et al. |
| 2019/0314176 A1 | 10/2019 | Nageswaran et al. |
| 2019/0314177 A1 | 10/2019 | Alonso et al. |
| 2019/0314179 A1 | 10/2019 | Nageswaran et al. |
| 2019/0336312 A1 | 11/2019 | Nageswaran et al. |
| 2019/0374358 A1 | 12/2019 | Nageswaran |
| 2020/0375769 A1 | 12/2020 | Nageswaran et al. |
| 2020/0405517 A1 | 12/2020 | Barooni |
| 2021/0196490 A1 | 7/2021 | Dawson et al. |
| 2022/0257396 A1 | 8/2022 | Ashby et al. |
| 2023/0029736 A1 | 2/2023 | Deen et al. |

FOREIGN PATENT DOCUMENTS

| | | |
|---|---|---|
| EP | 1344502 A2 | 9/2003 |
| JP | 2001504016 A | 3/2001 |
| JP | 2008518717 A | 6/2008 |
| JP | 2009542357 A | 12/2009 |
| JP | 2013500777 A | 1/2013 |
| JP | 2013158647 A | 8/2013 |
| WO | 9719713 A2 | 6/1997 |
| WO | 9820811 A1 | 5/1998 |
| WO | 2010127838 A2 | 11/2010 |
| WO | 2011076408 A1 | 6/2011 |
| WO | 2011081997 A1 | 7/2011 |
| WO | 2011122444 A1 | 10/2011 |
| WO | 2012158152 A1 | 11/2012 |
| WO | 2014074462 A2 | 5/2014 |
| WO | 2020072268 A1 | 4/2020 |

OTHER PUBLICATIONS

International Search Report and Written Opinion dated Oct. 15, 2020, International Application No. PCT/US20/70151, 110 pages.

Search Report dated Mar. 24, 2020, CN Application No. 201880007614.9, 10 pages.

Stoeckel, Dieter, et al., "Self-expanding nitinol stents: material and design considerations", Sep. 3, 2003, Springer-Verlag, pp. 292-301. (Year: 2003).

* cited by examiner

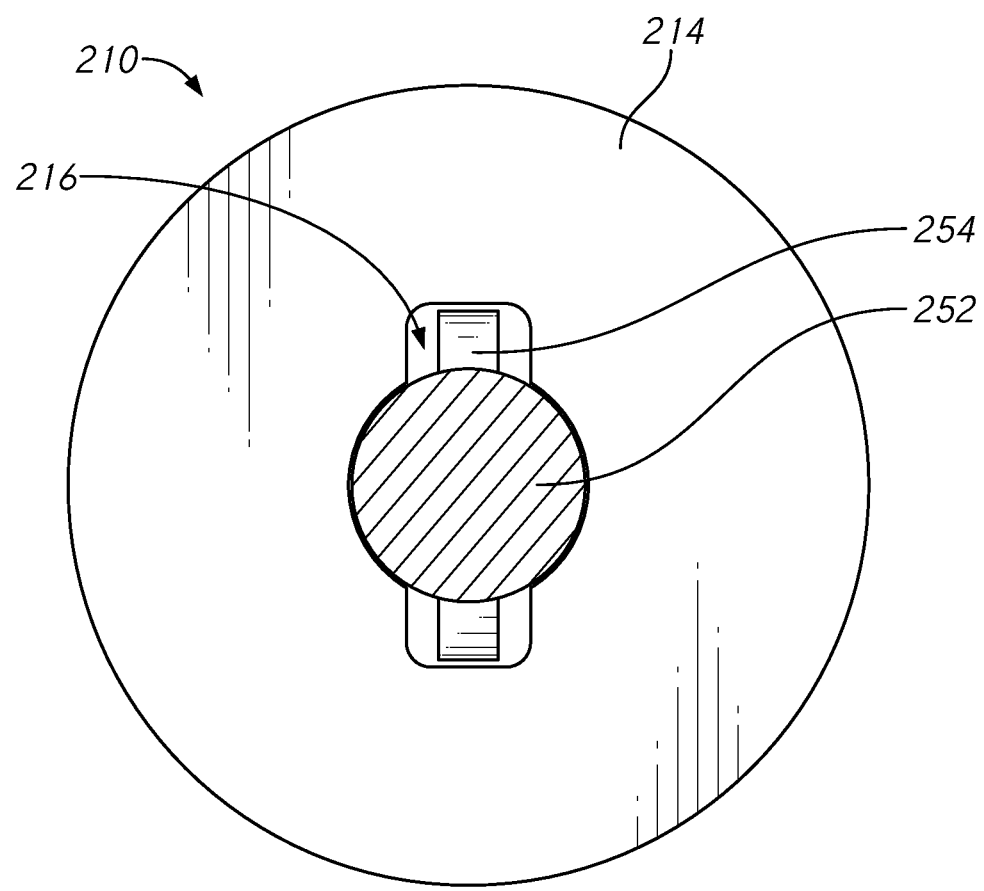
FIG. 5A1

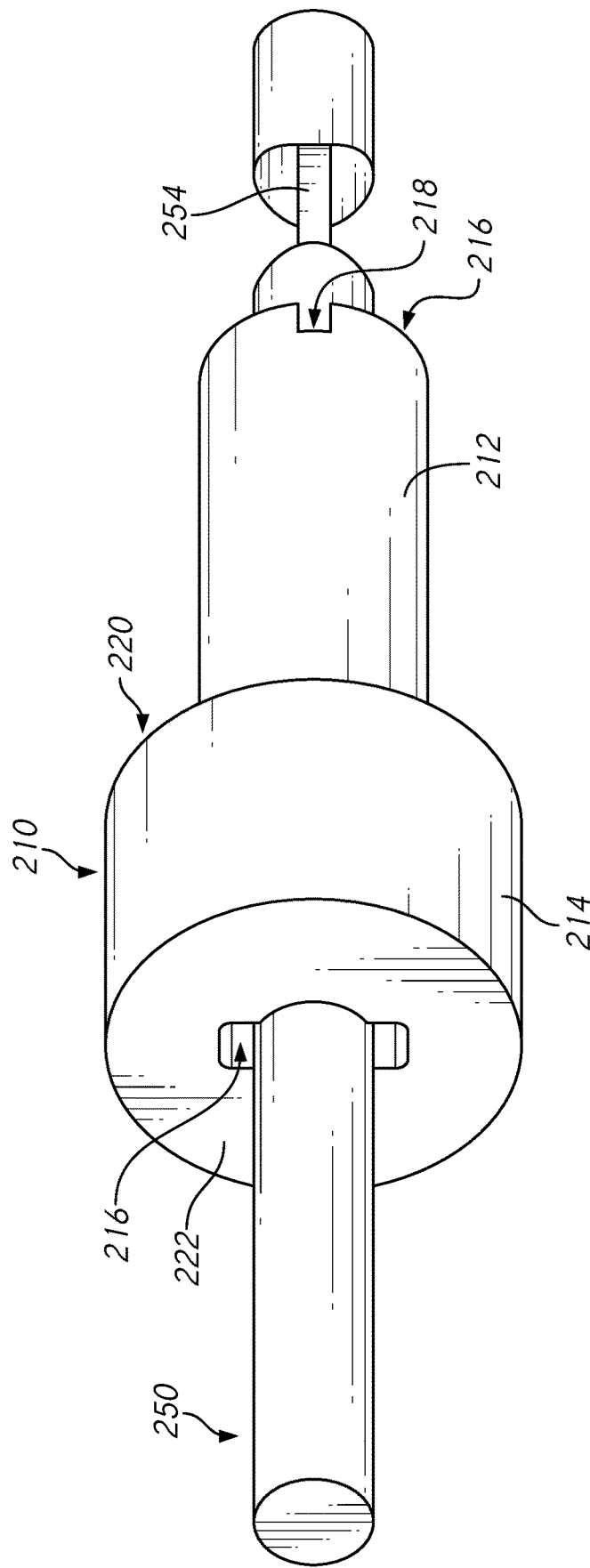

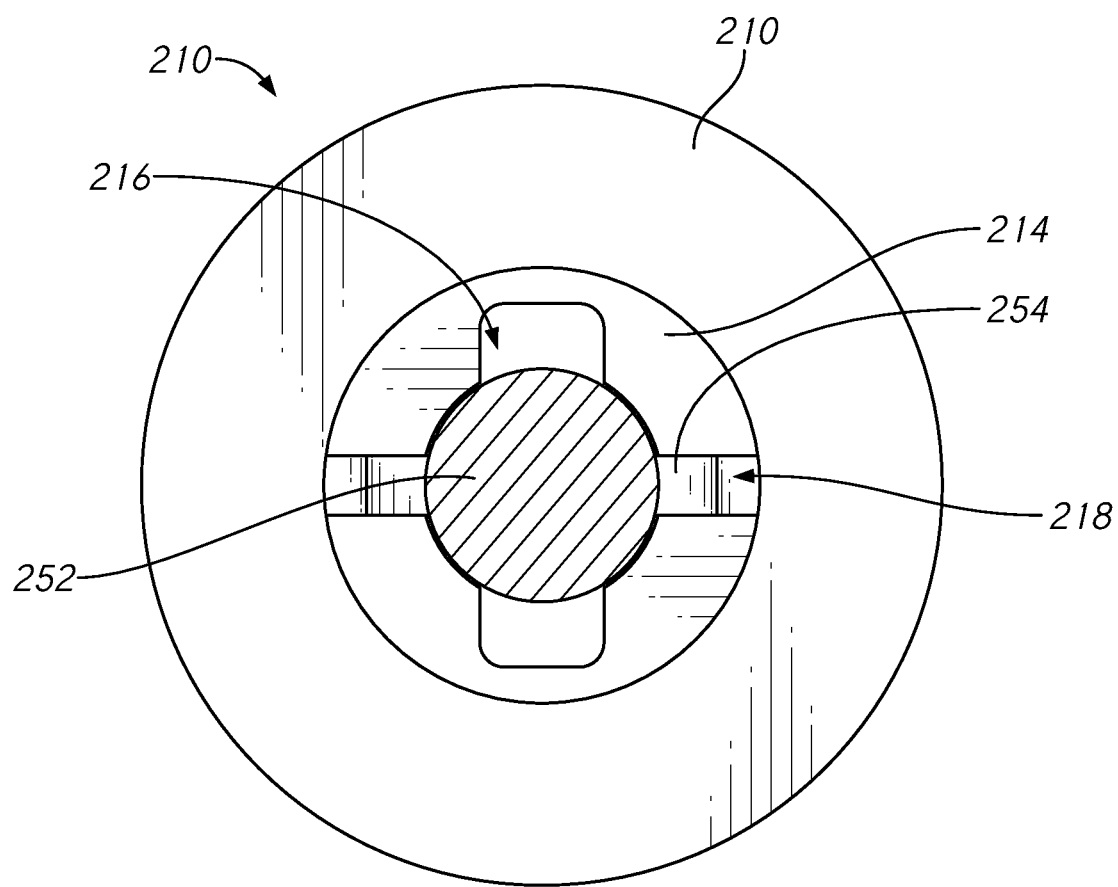
FIG. 5D1

MEDICAL DEVICE DELIVERY DEVICES, SYSTEMS, AND METHODS

TECHNICAL FIELD

The present technology relates to medical device delivery devices, systems, and methods.

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter is advanced through the distal region of the guiding catheter. A stent delivery system is then advanced out of the distal region of the guiding catheter into the vessel until the distal portion of the delivery system carrying the compressed stent is positioned at the point of the lesion within the vessel. The compressed stent is then released and expanded so that it supports the vessel at the point of the lesion.

SUMMARY

Conventional stent delivery systems can include a core member that assists with deploying a stent at a treatment site. The core member can be a multi-component assembly that includes a proximal portion in the form of a wire that can be gripped by a clinician, a middle portion in the form of a hypotube with flexibility enhancing cuts configured to extend through the patient's vasculature, and a distal portion in the form of a wire distally extending from a distal end of the hypotube. The stent can be positioned over the distal wire, where the stent can engage with the core member via one or more stent engagement members that are coupled to the distal wire. To ensure the stent is reliably and accurately deployed at the treatment site, the distal wire must be properly connected within the core member. The distal wire is typically connected within the core member by being soldered or welded to the hypotube. In these conventional stent delivery systems, the connection between the wire and the hypotube can fail. In severe cases, the distal wire can become disconnected from the hypotube and be left untethered from the rest of the delivery system while inside a blood vessel. These and other connection failures have been linked to the presence of flux within an inner diameter of the hypotube.

The present technology relates to medical delivery devices, systems, and methods configured to address the above-noted limitations of existing stent delivery systems as well as other issues. Some embodiments of the present technology, for example, are directed to a medical device delivery system comprising a joining element that can provide a stronger and more reliable connection between the wire and the hypotube within the core member. The joining element can be welded to an end of the hypotube and can interlock with the wire. This arrangement moves the solder location of the distal wire away from the interior of the hypotube and provides an interference fit for the distal wire instead of a soldered joint. As a result of this arrangement, the hypotube and distal wire within a core member are less susceptible to connection failures.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings. The subject technology is illustrated, for example, according to various aspects described below. These are provided as examples and do not limit the subject technology.

In one embodiment, a medical device delivery system is described. The medical device delivery system can include an elongated tubular member having a distal end portion, a proximal end portion, and a lumen extending therethrough and a joining element coupled to a distal end portion of the elongated tubular member. The joining element can include a bumper having a distal end portion configured to engage a proximal portion of a medical device and a proximal portion adjacent the distal end portion of the elongated tubular member, wherein the proximal portion defines a slot having a length along a first direction. The joining element can also include an aperture extending through the bumper, the aperture having a first cross-sectional dimension along a second direction and a second cross-sectional dimension along a third direction different from the second direction, the first cross-sectional dimension being greater than the second cross-sectional dimension, wherein the first direction is about orthogonal to the second direction. The medical device delivery system can also include an elongated shaft having a distal region and a flattened region proximal of the distal region, the flattened region having a greatest cross-sectional dimension that is smaller than the first cross-sectional dimension of the aperture but larger than the second cross-sectional dimension of the aperture, wherein the flattened region is at least partially received within the slot.

In one embodiment, a core assembly for a medical device delivery system is described. The core assembly can include an elongated tubular member having a distal end portion, a proximal end portion, and a lumen extending therethrough, and a joining element coupled to the distal end portion of the tubular member. The joining element can include: a bumper having a proximal face abutting the distal end portion of the elongated tubular member; a proximal portion extending proximal of the proximal face and into the lumen of the elongated tubular member; and an aperture extending through the bumper and the proximal portion, the aperture having a first cross-sectional dimension along a first radial axis and a second cross-sectional dimension along a second radial axis, the first cross-sectional dimension being greater than the second cross-sectional dimension. The core assembly can further include an elongated shaft coupled to the joining element. The elongated shaft can include: an intermediate portion extending distal to the bumper portion and configured to receive a medical device thereover; a proximal portion extending through the joining element aperture; and an engagement feature disposed along the proximal portion, the engagement feature having a first radially outermost dimension along a first radial direction and a second radially outermost dimension along a second radial direction, the first radially outermost dimension being smaller than the first cross-sectional dimension and the second-cross sectional dimension of the aperture, the second radially outermost dimension being smaller than the first cross-sectional dimension of the aperture but larger than the second cross-sectional dimension of the aperture.

In one embodiment, a medical device delivery system is described. The medical device delivery system can include a hypotube having a proximal portion, a distal portion, and a lumen extending therethrough and a joining element positioned at the distal portion of the hypotube. The joining element can include: a bumper portion having a proximal-facing surface abutting a distal end of the hypotube; a proximal portion extending proximally from the distal portion such that the proximal portion is positioned within the lumen of the hypotube; and an aperture extending through the bumper and proximal portions, wherein the aperture has a first cross-sectional dimension along a first radial direction and a second cross-sectional dimension along a second radial direction, the second cross-sectional dimension being smaller than the first cross-sectional dimension. The medical device delivery system can also include an elongated member having a proximally located attachment portion including a retention region extending through the aperture and a widened region extending laterally away from a longitudinal axis of the elongate member to a greater extent than the retention region, wherein the widened region is configured to fit through the aperture in a first orientation and to collide with the bumper and the proximal portions in a second orientation.

In one embodiment, a medical device delivery system is described. The medical device delivery system can include an elongated tubular member having a distal end portion, a proximal end portion, and a lumen extending therethrough, and a joining element coupled to a distal end portion of the elongated tubular member. The joining element can include: a bumper having a distal end portion configured to engage a proximal portion of a medical device and a proximal portion adjacent the distal end portion of the elongated tubular member; a nose having a body extending between a proximal end portion and a distal end portion, the proximal end portion of the nose being adjacent the distal end portion of the bumper; and an aperture extending through the bumper, the aperture having a first cross-sectional dimension along a first direction and a second cross-sectional dimension along a second direction different from the first direction, the first cross-sectional dimension being greater than the second cross-sectional dimension. The medical device delivery system can also include an elongated shaft having a distal region and a flattened region proximal of the distal region, the flattened region having a greatest cross-sectional dimension that is smaller than the first cross-sectional dimension but larger than the second cross-sectional dimension.

In one embodiment, a method of assembling a medical device delivery system is described. The method can include coupling a bumper to a distal end portion of an elongated tubular member. The bumper can include: a body having a proximal face abutting the distal end portion of the elongated tubular member and a distal face configured to abut a proximal portion of a medical device; a proximal portion extending proximal of the proximal face and into a lumen of the elongated tubular member, the proximal portion having a slot with a length along a first radial axis; and a aperture extending through the body and the proximal portion, the aperture having a first cross-sectional dimension along a second radial axis and a second cross-sectional dimension along a third radial axis, the first cross-sectional dimension being greater than the second cross-sectional dimension. The method can also include orienting an elongated shaft with the aperture. The elongated shaft can have an engagement feature disposed along a proximal portion of the elongated shaft, the engagement feature having a first radially outermost dimension along a first radial direction and a second radially outermost dimension along a second radial direction. Orienting the elongated shaft with the aperture can include aligning the second radial direction with the second radial axis. The method can also include moving the engagement feature of the elongated shaft distally through the first aperture; aligning the second radial direction with the first radial axis; and moving the engagement feature of the elongated shaft proximally until the engagement feature is received within the slot of the proximal portion of the bumper.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 5A1 is a cross-sectional view along the line 5A1 from FIG. 5A.

FIG. 5C is a schematic illustration of an elongated shaft being reoriented in accordance with one or more embodiments of the present technology.

FIG. 5D1 is a cross-sectional view along the line 5D1 from FIG. 5D.

DETAILED DESCRIPTION

The present technology relates to medical delivery devices, systems, and methods configured to address the above-noted limitations of existing stent delivery systems as well as other issues. Details of one or more embodiments of the technology are described below with reference to FIGS. 1-5E. As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device.

Figure 1A:
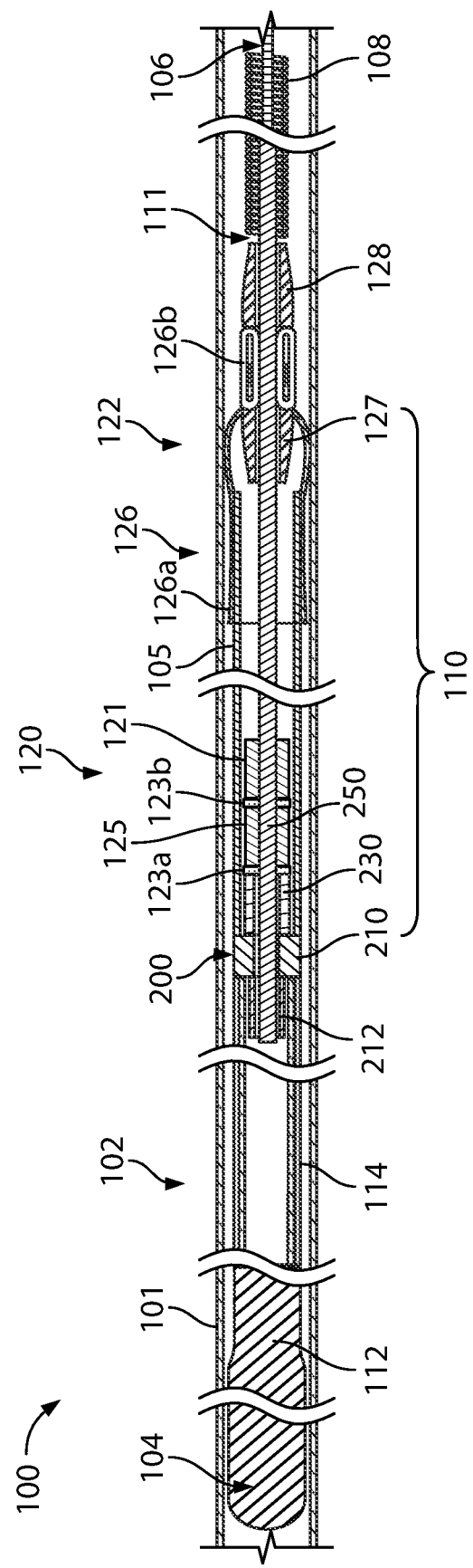
FIG. 1A is a schematic illustration of a medical device delivery system in accordance with one or more embodiments of the present technology.
Figure 1B:
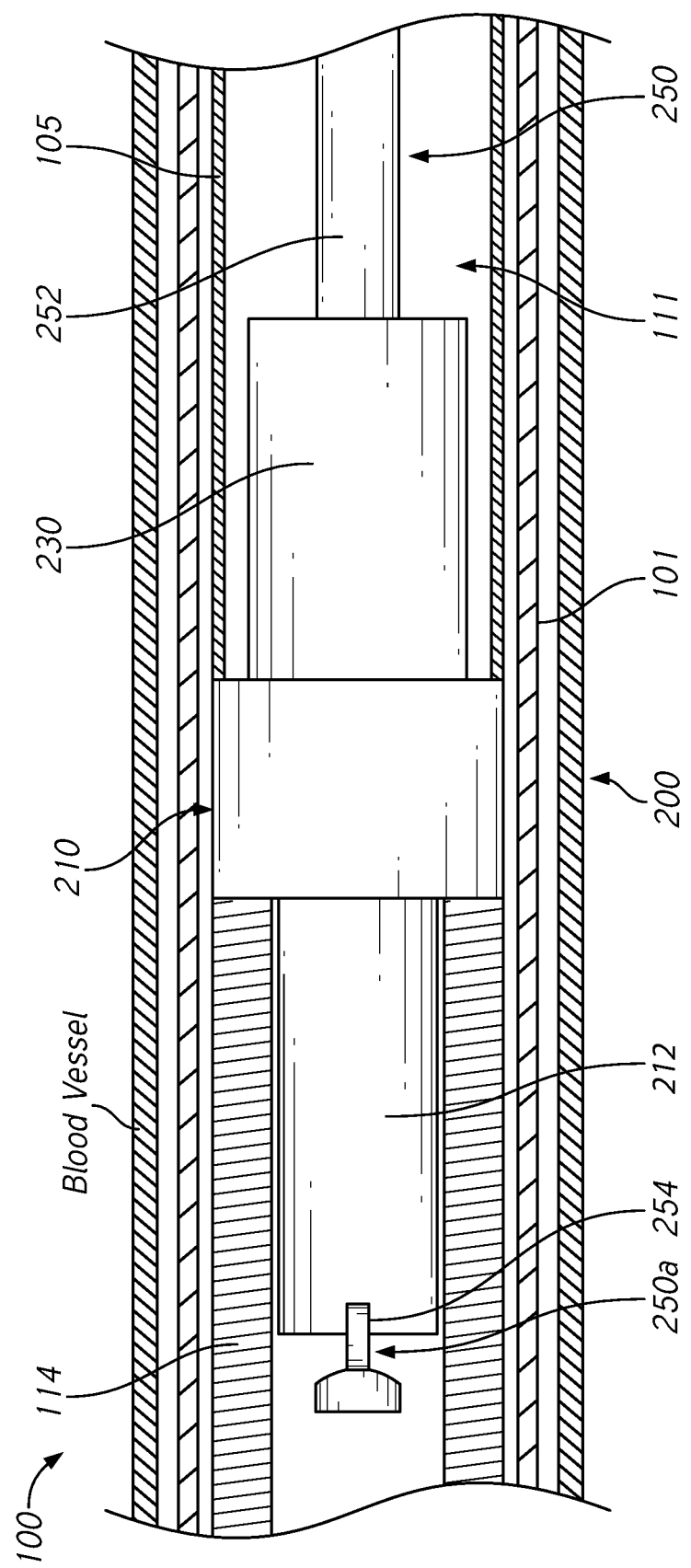
FIG. 1B is a partial schematic view of the medical device delivery system of FIG. 1A within a blood vessel.

FIG. 1A is a schematic illustration of a medical device delivery system 100 ("system 100") configured in accordance with one or more embodiments of the present technology. FIG. 1B is a partial schematic view of the medical device delivery system of FIG. 1A within a blood vessel. This system 100 may be used to deliver and/or deploy a medical device, such as but not limited to a stent, into a hollow anatomical structure, such as a blood vessel. The stent can comprise a braided stent or other form of stent such as a woven stent, knit stent, laser-cut stent, roll-up stent, etc. The stent can optionally be configured to act as a "flow diverter" device for treatment of aneurysms, such as those found in blood vessels including arteries in the brain or within the cranium, or in other locations in the body such as peripheral arteries. The stent can optionally be similar to any of the versions or sizes of the PIPELINE™ Embolization Device marketed by Medtronic Neurovascular of Irvine, California USA. The stent can alternatively comprise any suitable tubular medical device and/or other features, as described herein. In some embodiments, the stent can be any one of the stents described in U.S. application Ser. No. 15/892,268, filed Feb. 8, 2018, titled VASCULAR EXPANDABLE DEVICES, the entirety of which is hereby incorporated by reference herein and made a part of this specification.

With reference to FIGS. 1A and 1B, the system 100 can comprise a core member or core assembly 102 configured to extend generally longitudinally through the lumen 111 of an elongate catheter 101. The core member 102 can have a proximal region 104 and a distal region 106, which can optionally include a tip coil 108. The core member 102 can also comprise an intermediate portion 110 located between the proximal region 104 and the distal region 106. The intermediate portion 110 is the portion of the core member 102 onto or over which the stent 105 extends when the core member 102 is in the pre-deployment configuration as shown in FIG. 1A.

The delivery system 100 can include and/or be used with any number of catheters 101. For example, the catheter can optionally comprise any of the various lengths of the MARKSMAN™ catheter available from Medtronic Neurovascular of Irvine, California USA. The catheter can optionally comprise a microcatheter having an inner diameter of about 0.030 inches or less, and/or an outer diameter of 3 French or less near the distal region. Instead of or in addition to these specifications, the catheter can comprise a microcatheter which is configured to access the internal carotid artery, or another location within the neurovasculature distal of the internal carotid artery.

The core member 102 can generally comprise any member(s) with sufficient flexibility and column strength to move the stent 105 or other medical device through a surrounding catheter 101. The core member 102 can therefore comprise a wire, tube (e.g., hypotube), braid, coil, or other suitable member(s), or a combination of wire(s), tube(s), braid(s), coil(s), etc. The embodiment of the core member 102 depicted in FIG. 1A is of multi-member construction, comprising a wire 112 with a tube 114 surrounding the wire 112 along at least a portion of its length. For example, a distal portion of the wire 112 can be positioned within the tube 114 so that the tube 114 surrounds the distal portion of the wire 112. An outer layer of lubricious material such as PTFE (polytetrafluoroethylene or TEFLON™) or other lubricious polymers, can cover some or all of the tube 114 and/or wire 112. The wire 112 may taper or vary in diameter along some or all of its length. The wire 112 may include one or more fluorosafe markers (not shown), and such marker(s) can be located on a portion of the wire 112 that is not covered by the outer layer of lubricious material (e.g., proximal of the outer layer). This portion of the wire 112 marked by the marker(s), and/or proximal of any outer layer, can comprise a bare metal outer surface.

The core member 102 can comprise a stent coupling assembly 120 and/or a distal interface assembly 122 that can interconnect the stent 105 with the core member 102. In some embodiments, a joining element 200 couples the stent coupling assembly 120 and/or distal interface assembly 122 with the core member 102. As will be described in more detail, the joining element 200 can couple with the tube 114. For example, the joining element 200 can be welded to a distal end portion of the tube 114. The joining element 200 can be interlocked with an elongated shaft 250 that extends through the intermediate portion 110 and distal region 106 of the core member 102. The stent coupling assembly 120 can be coupled with the elongated shaft 250 within the intermediate portion 110 so that the stent coupling assembly 120 engages the stent 105. The distal interface assembly 122 can be coupled with the elongated shaft 250 distal to the stent 105 so that the distal interface assembly 122 engages with a distal portion of the stent 105.

The stent coupling assembly 120 can comprise one or more engagement members 123a, 123b (collectively "engagement members 123") that may underlie and mechanically engage or interlock with the stent 105. In this manner, the stent coupling assembly 120 cooperates with an overlying inner surface of a surrounding catheter 101 to engage the stent 105 such that the stent coupling assembly 120 can move the stent 105 along and within the catheter 101, e.g., as the user pushes the core member 102 distally and/or pulls the core member 102 proximally relative to the catheter 101, resulting in a corresponding distal and/or proximal movement of the stent 105 within the elongate shaft lumen 111.

The stent coupling assembly 120 can include one or more restraints 121 that are fixed to the core member 102 (e.g., to the elongated shaft 250 thereof in the depicted embodiment) so as to be immovable relative to the core member 102, either in a longitudinal/sliding manner or a radial/rotational manner. The stent coupling assembly 120 can also include a plurality of engagement members 123 separated by one or more spacers 125. For example, the stent coupling assembly 120 can include a first engagement member 123a and a second engagement member 123b separated by a spacer 125.

The engagement members 123 and/or the spacers 125 can be coupled to (e.g., mounted on) the core member 102 so that the stent coupling assembly 120 can rotate about the longitudinal axis of the core member 102 (e.g., of the intermediate portion 110), and/or move or slide longitudinally along the core member 102. For example, the engagement members 123 and the spacer 125 can be coupled to the elongated shaft 250 so that the engagement members 123 and the spacer 125 can rotate about the elongated shaft 250. In some embodiments, the stent 105 can be moved distally or proximally within an overlying catheter 101 via the stent coupling assembly 120. In some embodiments, the stent 105 can be resheathed via the stent coupling assembly 120 after partial deployment of the stent 105 from a distal opening of the catheter 101.

With continued reference to FIG. 1A, the distal interface assembly 122 can comprise a distal cover 126. In some examples, the distal cover 126 can take the form of, for example, a distal engagement member, a distal device cover, or distal stent cover. The distal cover 126 can be configured to reduce friction between the stent 105 (e.g., a distal portion thereof) and the inner surface of a surrounding catheter 101. For example, the distal cover 126 can be configured as a lubricious, flexible structure having a free first end or section 126a that can extend over at least a portion of the stent 105 and/or intermediate portion 110 of the core member 202, and a fixed second end or section 126b that can be coupled (directly or indirectly) to the core member 102. In some embodiments, the distal cover 126 is rotatably coupled to the core member 102.

The distal cover 126 can have a first (e.g., delivery) position, configuration, or orientation in which the distal cover 126 can extend proximally from the second section 126b or its (direct or indirect) attachment to the core member 102, and at least partially surround or cover a distal portion of the stent 105. The distal cover 226 can be movable from the first orientation to a second (e.g., resheathing) position, configuration, or orientation (not shown) in which the distal cover can be everted such that the first end 126a of the distal cover is positioned distally relative to the second end 126b of the distal cover 126 to enable the resheathing of the core member 102, either with the stent 105 carried thereby, or without the stent 105.

In some embodiments, the distal interface assembly can include a proximal and distal restraint 127, 128. One or both of the proximal and distal restraints 127, 128 can have an outside diameter or other radially outermost dimension that is smaller than the (e.g., pre-deployment) outside diameter or other radially outermost dimension of the distal cover 126, so that one or both of the restraints 127, 128 will tend not to bear against or contact the inner surface of the catheter 101 during operation of the core member 102. Alternatively, it can be preferable to make the outer diameters of the restraints 127 and 128 larger than the largest radial dimension of the pre-deployment distal cover 126, and/or make the outer diameter of the proximal restraint 127 larger than the outer diameter of the distal restraint 128. This configuration allows easy and smooth retrieval of the distal cover 126 and the restraints 127, 128 back into the elongate shaft post stent deployment.

The distal cover 126, the proximal restraint 127, and the distal restraint 128 can be coupled to (e.g., mounted on) the core member 102 so distal interface assembly can rotate about the longitudinal axis of the core member 102. In embodiments of the core member 102 that employ both a rotatable stent coupling assembly 120 and a rotatable distal cover 126, the stent 105 can be rotatable with respect to the core member 102 about the longitudinal axis thereof, by virtue of the rotatable connections of the stent coupling assembly 120 and distal cover 126. In such embodiments, the stent 105, stent coupling assembly 120 and distal cover 126 can rotate together in this manner about the core member 102. When the stent 105 can rotate about the core member 102, the core member 102 can be advanced more easily through tortuous vessels as the tendency of the vessels to twist the stent 105 and/or core member 102 is negated by the rotation of the stent 105, stent coupling assembly 120, and distal cover 126 about the core member 102. In addition, the required push force or delivery force is reduced, as the user's input push force is not diverted into torsion of the stent 105 and/or core member 102. The tendency of a twisted stent 105 and/or core member 102 to untwist suddenly or "whip" upon exiting tortuosity or deployment of the stent 105, and the tendency of a twisted stent to resist expansion upon deployment, are also reduced or eliminated. Further, in some such embodiments of the core member 102, the user can "steer" the core member 102 via the tip coil 108, particularly if the coil 108 is bent at an angle in its unstressed configuration. Such a coil tip can be rotated about a longitudinal axis of the system 100 relative to the stent 105, coupling assembly 120 and/or distal cover 126 by rotating the distal region 106 of the core member 102. Thus, the user can point the coil tip 108 in the desired direction of travel of the core member 102, and upon advancement of the core member the tip will guide the core member in the chosen direction.

With reference to FIGS. 1A and 1B, the joining element 200 can include a bumper portion or bumper 210, a proximal portion 212 proximal to the bumper 210, and a nose portion or nose 230 distal of the bumper 210. The elongated shaft 250 can extend through a lumen of the joining element 200 and extend distally to the nose portion 230. As discussed in more detail below, the elongated shaft 250 can mechanically interlock with the proximal portion 212 of the joining element 200, thereby securing the elongated shaft 250 in position relative to the joining element 200. As noted previously, the stent engagement members 123, spacer 125, and distal restraint 121 can be mounted over the elongated shaft 250 at a position distal to the joining element 200. In some embodiments, the stent 105 can be disposed over the stent engagement members 123 with a proximal end of the stent 105 abutting the distal face of the bumper 210. In this configuration, the nose portion 230 can extend partially into a lumen of the stent 105.

The bumper 210 can have an outer diameter that is slightly smaller than the inner diameter of the catheter 101, leaving a radial gap between an outer edge of the bumper 210 and the inner wall of the catheter 101. The nose 230 can have a diameter that is slightly smaller than an inner diameter of a compressed stent 105, allowing for the nose 230 to be positioned within a lumen formed by the stent 105. As previously noted, the joining element 200 can be coupled with the tube 114. The joining element 200 can couple to a distal end portion of the tube 114 so that the bumper 210 is axially disposed between the tube 114 and the stent 105. For example, the distal end portion of the tube 114 can be welded, soldered, and/or otherwise joined to a proximal face 220 of the bumper 210 while the stent 105 is disposed distal to a distal face 222 of the bumper 210. In some embodiments, when the joining element 200 is coupled to the tube 114, the proximal portion 212 of the bumper 210 can be disposed within a lumen formed by the tube 114. In various embodiments, the joining element 200 is configured to abut the proximal end or proximal edge of the stent 105. For example, the bumper 210 can be positioned adjacent the stent 105 so that the bumper 210 abuts the proximal end of the stent 105.

The joining element 200 can couple with the elongated shaft 250. For example, the elongated shaft 250 can interlock with the proximal portion 212 of the joining element 200 and extend through the joining element 200. In some embodiments, the elongated shaft 250 can be coupled with the nose 230 of the joining element 200. For example, the elongated shaft 250 can be welded, soldered, and/or otherwise joined with the nose 230. A portion of the elongated shaft 250 that is distal to the bumper 210 can be configured to receive a medical device such as a stent thereover. For example, the stent coupling assembly 120 can couple to the elongated shaft 250 at a position that is distal to the bumper 210, with the stent coupling assembly 120 configured to engage the stent 105 over this portion of the elongated shaft 250.

As will be described in more detail, the elongated shaft 250 can include a widened region 254 that interlocks with the proximal portion 212 of the joining element 200. By interlocking the elongated shaft 250 with the bumper 210, the joining element 200 can retain the elongated shaft 250 and prevent the elongated shaft 250 from moving distally relative to the core member 102. In some embodiments, the nose 230 can be coupled with the elongated shaft 250 in a manner that prevents the elongated shaft 250 from moving proximally relative to the core member 102. For example, the nose 230 can be welded, soldered, and/or otherwise joined with the elongated shaft 250 so that the elongated shaft 250 cannot be moved proximally relative to the core member 102. Together, the mechanical interlock at the proximal portion 212 of the joining element 200 and the solder joint at the nose 230 of the joining element 200 can prevent any axial movement of the elongated shaft 250 relative to the joining element 200 and/or the tube 114. Additionally, or alternatively, the bumper 210 and the nose 230 can prevent any rotational movement of the elongated shaft 250 relative to the joining element 200 and/or the tube 114. Accordingly, coupling the elongated shaft 250 with the joining element 200 can render the elongated shaft 250 immovable relative to the joining element 200 and/or the tube 114, as the joining element 200 can retain the elongated shaft 250 in place axially and rotationally.

In some embodiments, the joining element 200 can be used to move (e.g., push) the stent 105 distally through the catheter 101. For example, in response to a distal push force applied to the core member 102, the distal face 222 of the bumper 210 can press against the stent 105 and move the stent 105 distally within the catheter 101. When the joining element 200 is configured to push the stent 105 distally, the joining element 200 can be configured to transmit some, most, or all of a distally directed axial (e.g., push) force to the stent 105, wholly or partially in place of the engagement members 123. In such a configuration, the engagement members 123 can be configured to transmit little or no push force to the stent 105 while the stent 105 is delivered distally along the length of the catheter 101. Advantageously, this can reduce or eliminate a tendency of the engagement members 123 to distort the pores of the stent 105 with which the engagement members 123 are engaged when the engagement members 123 are employed to transmit force to and move the stent 105 within the catheter 101. Use of the joining element 200 to move the stent 105 in this manner can also reduce or eliminate axial movement of the stent 105 relative to the core member 102 that sometimes accompanies the pore distortion. In most cases, the vast majority of the travel of the stent 105 within the catheter 101 is in the distal or "push" direction during delivery to the treatment location, in contrast to the relatively short travel involved in resheathing the stent 105, in the proximal or "pull" direction, prior to an eventual final deployment of the stent. Therefore, configuring the joining element 200 to transmit most or all of the push force to the stent 105 can significantly reduce or substantially eliminate such distortion and/or relative axial movement of the stent.

Figure 2A:
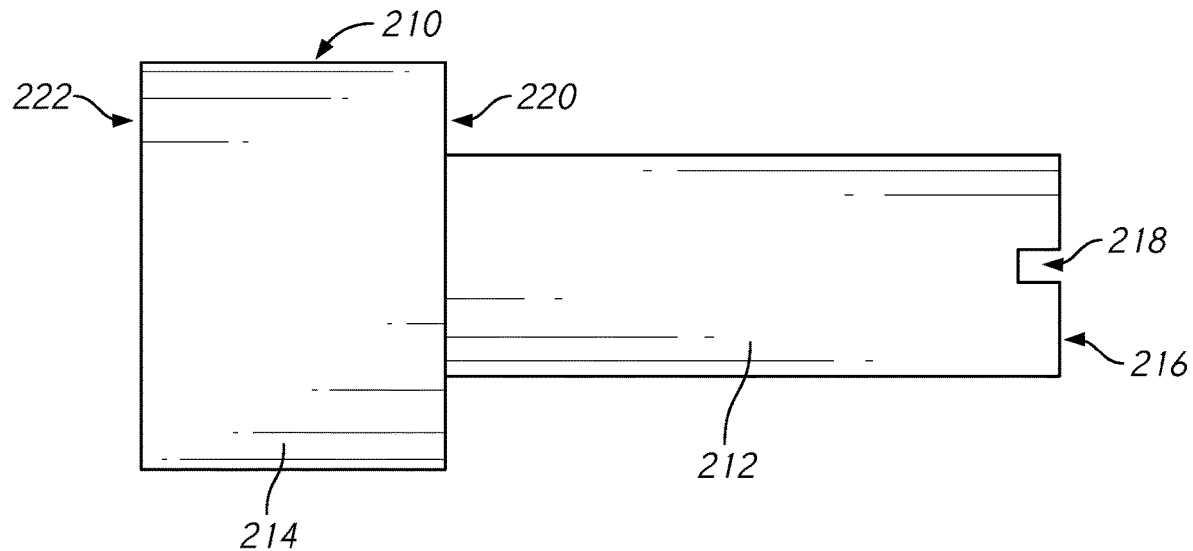
FIG. 2A is a schematic illustration of a bumper in accordance with one or more embodiments of the present technology.
Figure 2B:
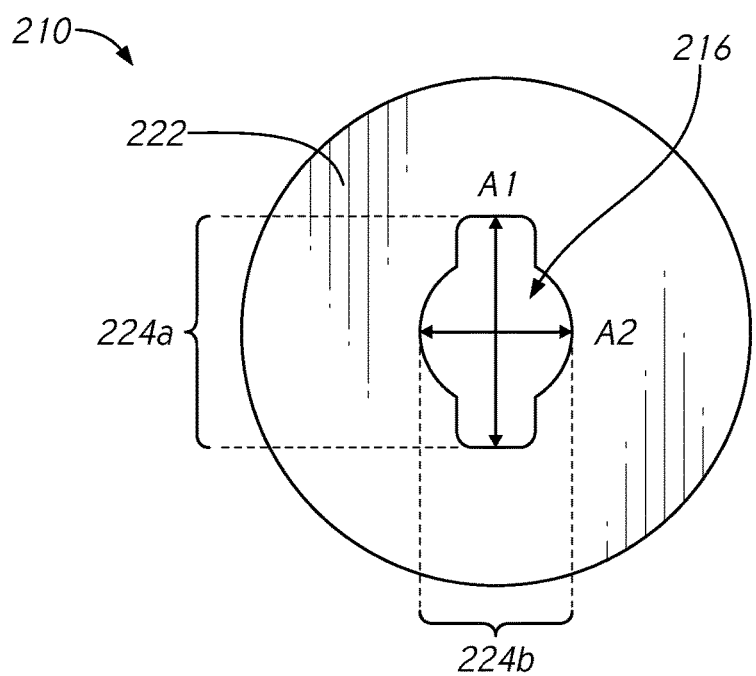
FIG. 2B is an end view of the bumper of FIG. 2A.

FIG. 2A illustrates a schematic view of the bumper 210 in accordance with one or more embodiments of the present technology. FIG. 2B illustrates an end view of the bumper 210 from FIG. 2A. Referring to FIGS. 2A and 2B together, the bumper 210 can include a generally cylindrical body 214 disposed at the distal end of the proximal portion 212. Although some examples describe the proximal portion 212 as being separate distinct from the bumper 210, in some embodiments the proximal portion 212 and the bumper 210 can be integrally formed and/or combined into the same component. For example, the bumper 210 can define the proximal portion 212 and can include a slot 218 (described below) configured to mechanically interlock with the elongated shaft 250. The proximal portion 212 forms a cylindrical body that extends proximally from the proximal face 220 of the bumper 210. In some embodiments, the width of the proximal portion 212 is smaller than an inner diameter of the tube 114, allowing for the proximal portion 212 to be received within the tube 114. The body 214 of the bumper 210 can have a generally a cylindrical shape that is wider (e.g., having a greater radially outermost dimension) than the proximal portion 212 and can have a width that is slightly smaller than the inner diameter of the catheter 101, leaving a radial gap between an outer edge of the body 214 and the inner wall of the catheter 101. Additionally, the bumper 210 can define both the proximal face 220 and a distal face 222. An aperture 216 can be formed through the bumper 210 and the proximal portion 212. The aperture 216 can form an irregular shaped lumen throughout the bumper 210 and the proximal portion 212. For example, as illustrated in FIG. 2B, one portion of the aperture 216 can form a rectangular or slot profile while a second portion of the aperture 216 can form a circular or ellipsoid profile. These separate portions of the aperture can define one or more cross-sectional dimensions of different lengths. For example, the slot portion can define a first cross-sectional dimension that has a length 224a and the circular portion can define a second cross-sectional dimension that has a length 224b. In various embodiments, the length 224a can be larger than the length 224b. Additionally, or alternatively, the aperture 216 can define two radial axes or directions. For example, as illustrated in FIG. 2B, the aperture 216 defines a first radial axis A1 along the rectangular profile and a second radial axis A2 along the circular profile. In some embodiments, a slot 218 can be formed at the proximal end of the proximal portion 212. The slot 218 can form a channel within the proximal portion 212 that insects with the aperture 216. In various embodiments, the slot 218 can have a length that is formed at an angle with respect to the axis A1. For example, the slot 218 can be perpendicular to the axis A1. In some embodiments, the slot 218 can have a length that is parallel to the axis A2.

As previously noted, the bumper 210 and the proximal portion 212 can couple with the elongated shaft 250. The aperture 216 and can be sized so that the elongated shaft 250 can be received within the aperture 216. As will be described in more detail, the widened region 254 of the elongated shaft 250 can be positioned within slot 218. Positioning the widened region 254 within the slot 218 interlocks the elongated shaft 250 with the joining element 200 and prevents the elongated shaft 250 from moving distally and/or rotationally relative to the joining element 200.

Figure 3A:
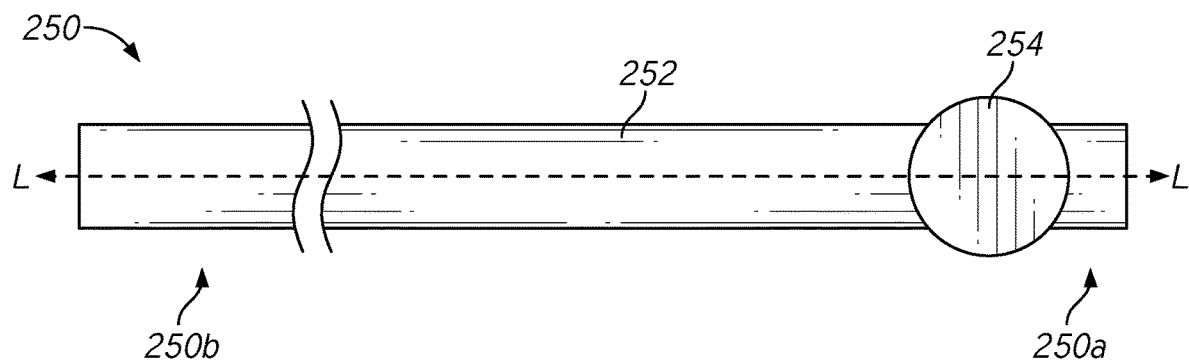
FIG. 3A is a schematic illustration of an elongated shaft in accordance with one or more embodiments of the present technology.
Figure 3B:
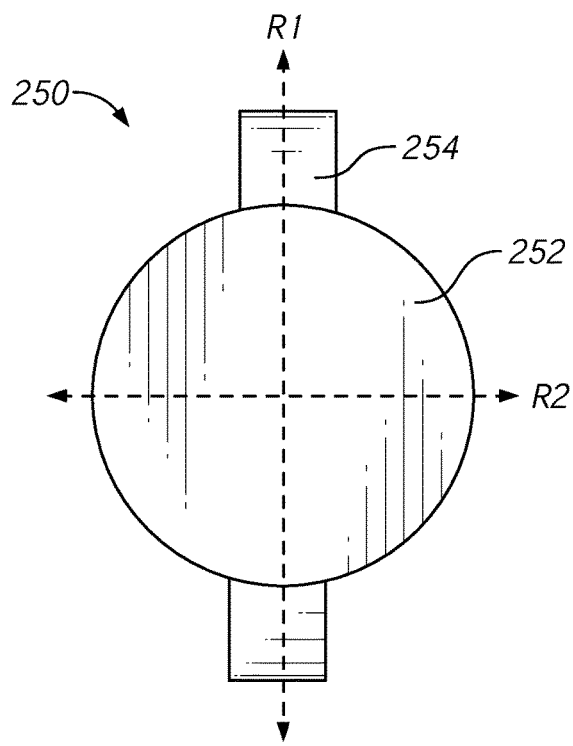
FIG. 3B is an end view of the elongated shaft of FIG. 3A.

FIG. 3A illustrates a schematic view of the elongated shaft 250 in accordance with one or more embodiments of the present technology. FIG. 3B illustrates an end view of the elongated shaft 250 of FIG. 3A. Referring to FIGS. 3A and 3B together, the elongated shaft 250 can include a body 252 and a widened region 254. The body 252 can extend along an axis L and define a proximal portion 250a and a distal portion 250b. At or proximate the proximal portion 250a, the widened region 254 can be formed in the body 252.

The widened region 254 can be a flattened or "coined" region of the body 252 that forms a cylindrical profile which is normal to a cylindrical profile formed by the body 252. For example, as illustrated in FIGS. 3A and 3B, body 252 forms a cylindrical profile having a height along the axis L while the widened region 254 forms a cylindrical profile having a height along a radial direction R2, with the radial direction R2 being normal to the axis L. This profile of the widened region 254 results in the widened region 254 having cross-sectional dimension that is greater than a cross-sectional dimension of the body 252 along one direction but less than a cross-sectional dimension the body 252 along a separate direction. For example, as illustrated in FIG. 3B, the greatest cross-section dimension of the widened region 254 is greater than greatest cross-section dimension of the body 252 along a radial direction R1 but smaller than greatest cross-section dimension of the body 252 along the radial direction R2. In some embodiments, the widened region 254 can be radially wider than the body 252 along one direction but having substantially the same radial dimension as the body 252 along another direction. In some embodiments, the widened region 254 can include one or more projections (e.g., ridges, bumps, projections, etc.) that project radially outward from the surface of the body 252 at the widened region 254.

The elongated shaft 250 can be sized so that the elongated shaft 250 can be received within the aperture 216. For example, the body 252 of the elongated shaft 250 can have a diameter that is smaller than the length 224b of the aperture 216 while the widened region 254 can have a diameter that is smaller than the length 224a of the aperture 216. By being sized in this manner, both the body 252 and the widened region 254 of the elongated shaft 250 can be received within the aperture 216 of the bumper 210 or proximal portion 212. In some embodiments, the elongated shaft 250 can be received within the aperture 216 when the elongated shaft 250 is in a specific orientation. For example, the widened region 254 can have a diameter that is greater than the length 224b, preventing the widened region 254 from moving through the bumper 210 or proximal portion 212 when the radial direction R1 aligns with the axis A2, but allowing the widened region 254 to move through the bumper 210 or proximal portion 212 when the radial direction R1 aligns with the axis A1. Additionally or alternatively, the widened region 254 can be positioned within the slot 218. The slot 218 can be sized to form a friction fit with widened region 254. When the widened region 254 is positioned within the slot 218, the elongated shaft 250 is prevented from moving distally and/or rotating until the widened region 254 is removed from the slot 218.

The widened region 254 of the elongated shaft 250 can be formed by crimping or crushing a portion of the elongated shaft 250. For example, a press can press into a portion of the elongated shaft 250, forming the widened region 254. The widened region 254 can be formed at any suitable location along the length of the elongated shaft 250, including at a proximalmost end of the shaft 250 or at a region spaced apart from the proximalmost end.

In some embodiments, the widened region 254 can take the form of an engagement feature. The engagement feature can define a first radially outermost dimension along the radial direction R2 and a second radially outermost dimension along the second radial direction R1. In some embodiments, the first radially outermost dimension is smaller than the length 224a of the first cross-sectional dimension and the length 224b of the second-cross sectional dimension. In various embodiments, the second radially outermost dimension is smaller than the length 224a of the first cross-sectional dimension but larger than the length 224b of the second cross-sectional dimension. This configuration allows for the widened region 254 to be moved through the aperture 216 when the widened region 254 is aligned with second cross-sectional dimension (e.g., when the radial direction R1 aligns with the axis A1).

In some embodiments, the widened region 254 of the elongated shaft 250 can take the form of an attachment portion and the portion of the elongated shaft 250 extending through the bumper 210 can take the form of a retention region. The attachment portion of the elongated shaft 250 can extend laterally away from an axis L of the elongated shaft 250 to a greater extent than the retention region of the elongated shaft 250. In some embodiments, the attachment portion is configured to fit through the aperture 216 in a first orientation and to collide with the bumper 210 or proximal portion 212 in a second orientation. For example, when the attachment portion is aligned with the larger portion of the aperture 216, the attachment portion can fit within the aperture 216, but when the attachment portion is not aligned with the larger portion of the aperture 216, the attachment portion will collide with the distal face 222 of the bumper 210 or the proximal face of the proximal portion 212.

Figure 4A:
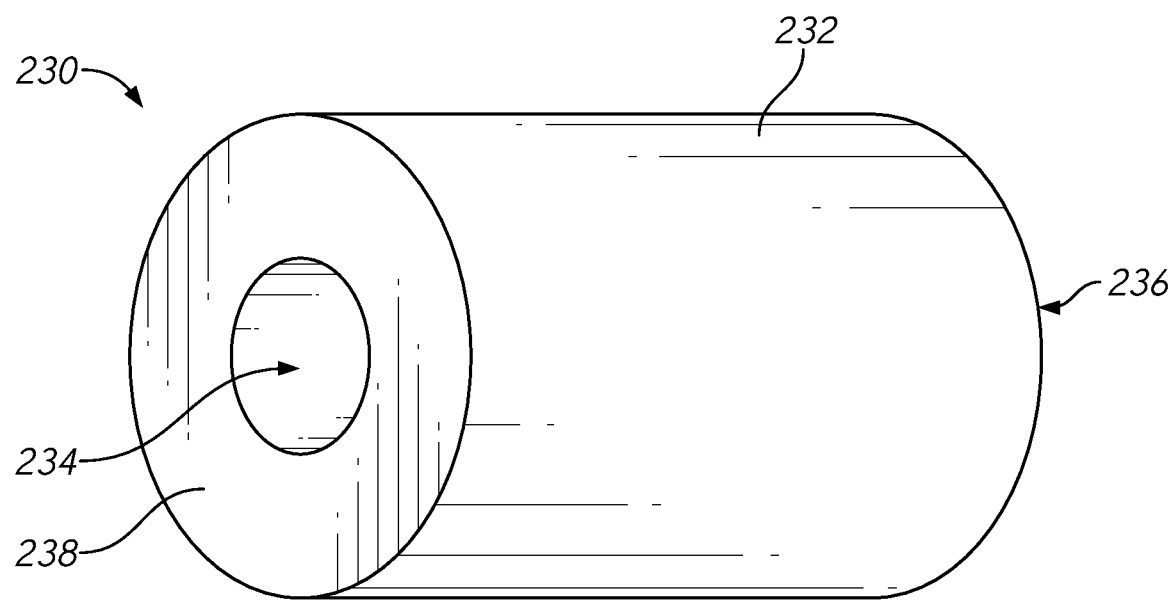
FIG. 4A is a schematic illustration of a nose in accordance with one or more embodiments of the present technology.
Figure 4B:
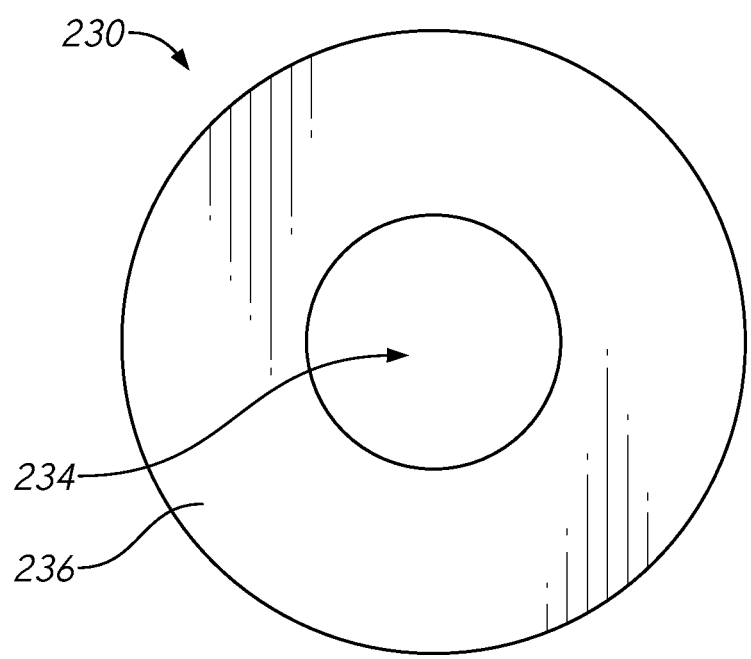
FIG. 4B is an end view of the nose of FIG. 4A.

FIG. 4A illustrates an isometric view of the nose 230 in accordance with one or more embodiments of the present technology, and FIG. 4B illustrates a view of a proximal face 236 of the nose 230. Referring to FIGS. 4A and 4B together, the nose 230 can have a body 232 with an aperture 234 extending through the body 232. The body 232 can form a cylindrical profile with a proximal face 236 at a first end and a distal face 238 at a second end opposite the first. The diameter or width of the body 232 can be less than the diameter or width of the stent 105, allowing for the nose 230 to be positioned within the lumen of the stent 105 without contacting the stent 105.

As previously noted, the nose 230 can be positioned distal of the bumper 210. In some embodiments, the proximal face 236 of the nose 230 can contact the distal face 222 of the bumper 210. In various embodiments, the nose 230 can be coupled to the bumper 210. For example, the nose 230 can be welded, soldered, or otherwise joined to the bumper 210. Additionally, or alternatively, the nose 230 can be coupled with the elongated shaft 250. At least a portion of the elongated shaft 250 can be disposed within the aperture 234 of the nose 230. While disposed within the aperture 234, the elongated shaft can be welded, soldered, or otherwise joined with the nose 230. In some embodiments, the aperture 216 can align with the aperture 234.

By coupling the nose 230 with the elongated shaft 250, the axial movement of the elongated shaft 250 can be limited or prevented. For example, the elongated shaft 250 can be prevented from moving proximally relative to the core member 102, as the nose 230 would collide with the bumper 210, stopping the elongated shaft 250 from moving proximally. Additionally, or alternatively, the nose 230 can prevent the elongated shaft 250 from rotating relative to the core member 102. For example, the coupling the nose 230 with the bumper 210 and the elongated shaft 250 can stop any rotational movement of the elongated shaft 250 relative to the core member 102. In some embodiments, coupling the nose 230 with the bumper 210 and the elongated shaft 250 can prevent any axial movement of the elongated shaft 250 relative to the core member 102. For example, a fixed connection between the nose 230, bumper 210, and elongated shaft 250 can render the elongated shaft 250 immovable relative to the core member 102.

Figure 5A:
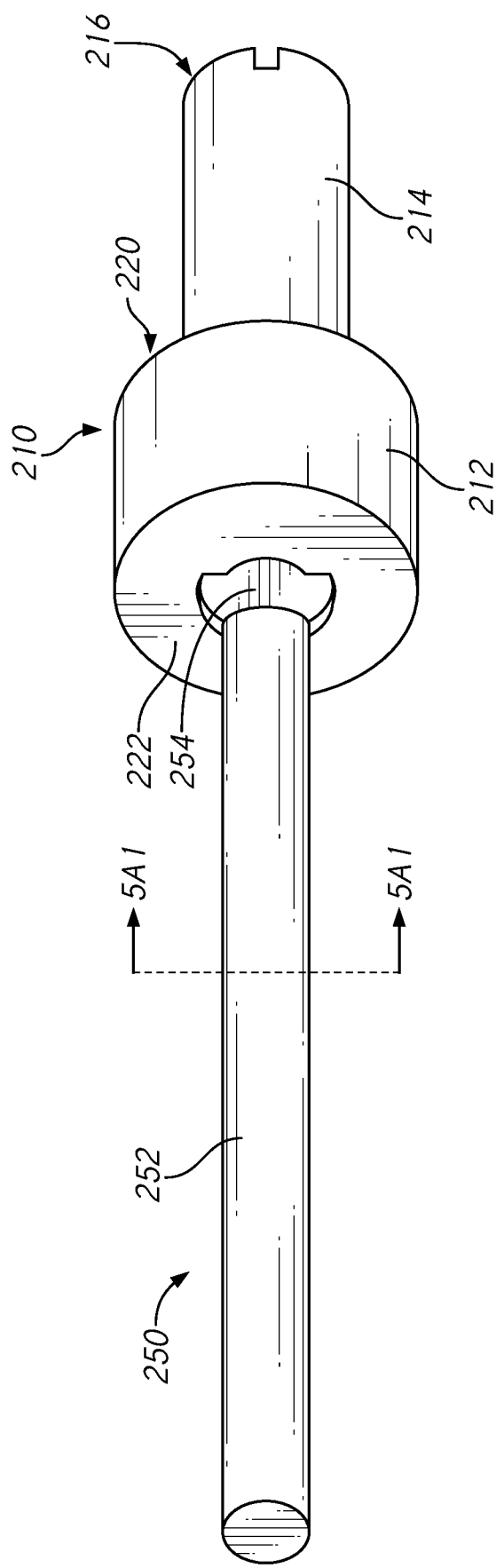
FIG. 5A is a schematic illustration of an elongated shaft being inserted into a bumper in accordance with one or more embodiments of the present technology.

FIGS. 5A-5E illustrate several schematic views of interlocking the elongated shaft 250 with the joining element 200, in accordance with one or more embodiments of the present technology. FIG. 5A illustrates the elongated shaft 250 being inserted into the aperture 216 of the bumper 210 and FIG. 5A1 shows a cross-sectional view of FIG. 5A along the 5A1 line within FIG. 5A. As illustrated in FIG. 5A, the elongated shaft 250 is inserted into the aperture 216 of the bumper 210 at the distal face 222 of the bumper 210. In some embodiments, the elongated shaft 250 can be inserted into the proximal face of the proximal portion 212. While being inserted into the bumper 210 the widened region 254 is oriented so that the radial direction R1 of the elongated shaft 250 aligns with the axis A1 of the aperture 216. This orientation allows for the widened region 254 to inserted into the aperture 216 without the bumper 210 impeding its movement, as illustrated in FIG. 5A1.

Figure 5B:
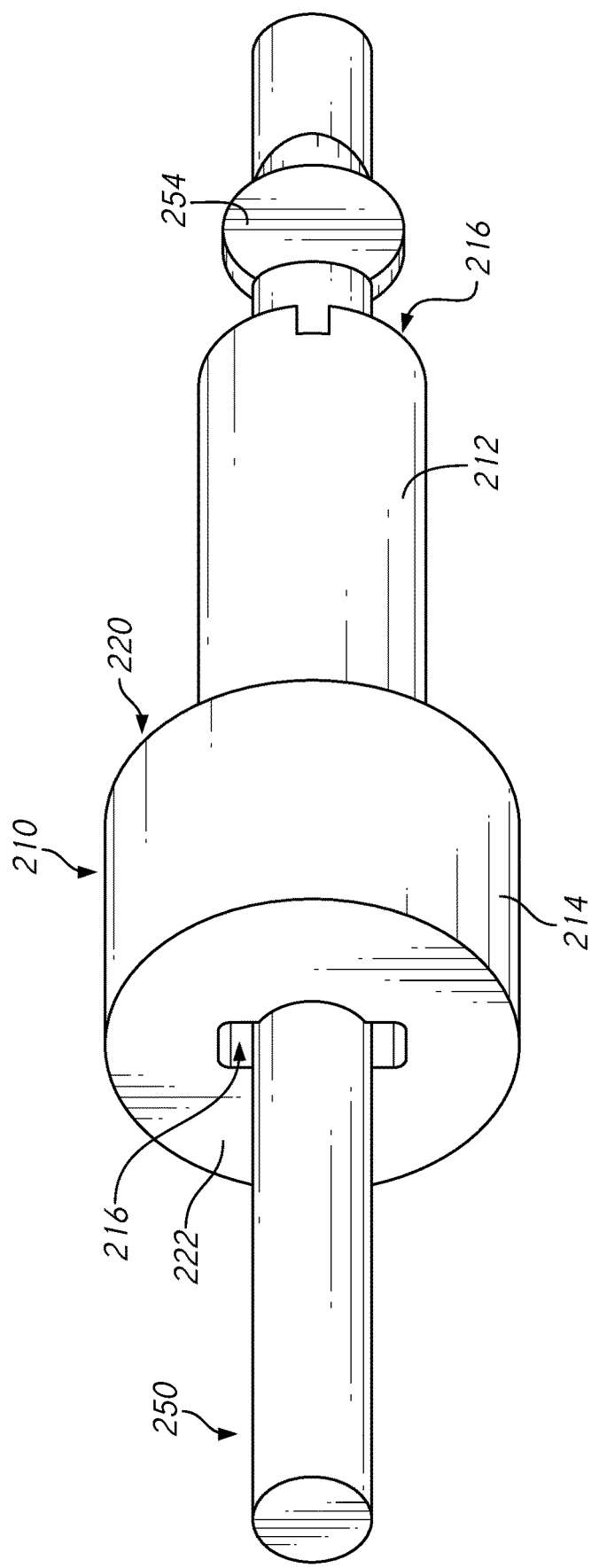
FIG. 5B is a schematic illustration of an elongated shaft inserted into a bumper in accordance with one or more embodiments of the present technology.

FIG. 5B illustrates the elongated shaft 250 being received in the aperture 216 of the bumper 210 and proximal portion 212 with the widened region 254 being positioned proximal of the proximal portion 212. The elongated shaft 250 can be proximally pushed through the aperture 216 until the widened region 254 is positioned proximally of the proximal portion 212. In this position, the widened region 254 can be spaced apart from the bumper 210, allowing for the elongated shaft 250 to be rotated freely and relative to the bumper 210.

FIG. 5C illustrates the elongated shaft 250 being reoriented after the widened region 254 is positioned proximal of the proximal portion 212. After the widened region 254 is pushed through the aperture 216, and the elongated shaft 250 is free to rotate, the elongated shaft 250 can be aligned with the slot 218. As previously noted, the slot 218 can be formed at an angle with respect the axis A1. Accordingly, to align the widened region 254 with the slot 218, the widened region is rotated so that the radial direction R1 aligns with the length of slot 218. Aligning the widened region 254 with the slot 218 prevents the elongated shaft 250 from being axially moved through the joining element 200, as the widened region 254 will collide with proximal portion 212 and impede any movement through the aperture 216.

Figure 5D:
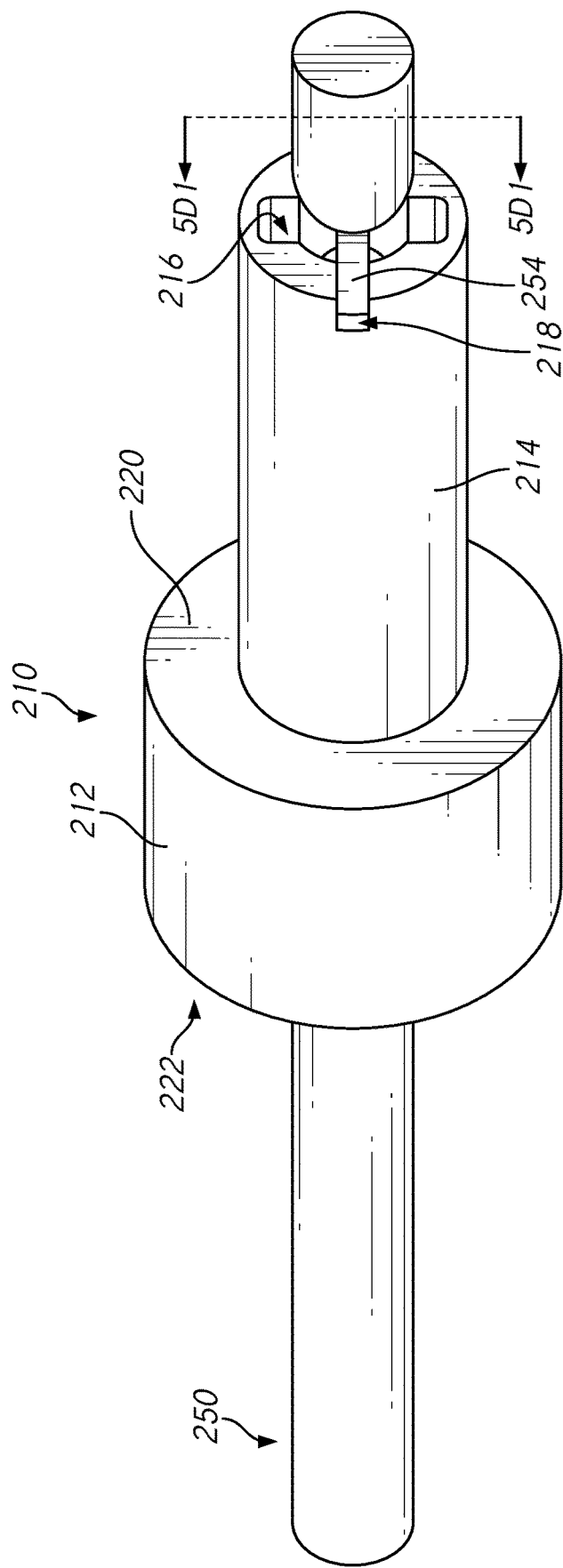
FIG. 5D is a schematic illustration of a widened region being received within a slot in accordance with one or more embodiments of the present technology.

FIG. 5D illustrates the elongated shaft 250 interlocked with the proximal portion 212 and FIG. 5D1 shows a cross-sectional view of FIG. 5D along the 5D1 line within FIG. 5D. After the elongated shaft 250 is reoriented so that the widened region 254 is aligned with the slot 218, the elongated shaft 250 can be moved distally so the widened region 254 is received within the slot 218, as illustrated in FIGS. 5D and 5D1. With the widened region 254 being received within the slot 218, the elongated shaft 250 is prevented from moving further distally relative to the proximal portion 212, as the widened region 254 of the elongated shaft 250 is unable to move through the aperture 216 while positioned within the slot 218. Additionally, or alternatively, when the widened region 254 is received within the slot 218, the elongated shaft 250 is prevented from rotating relative to the joining element 200, as the fit between the widened region 254 and slot 218 prevents any substantial rotational movement of the elongated shaft 250 independent from the bumper 210. In some embodiments, the elongated shaft 250 can later be adjusted axially and/or rotationally after the elongated shaft 250 is moved proximally out of the slot 218.

Figure 5E:
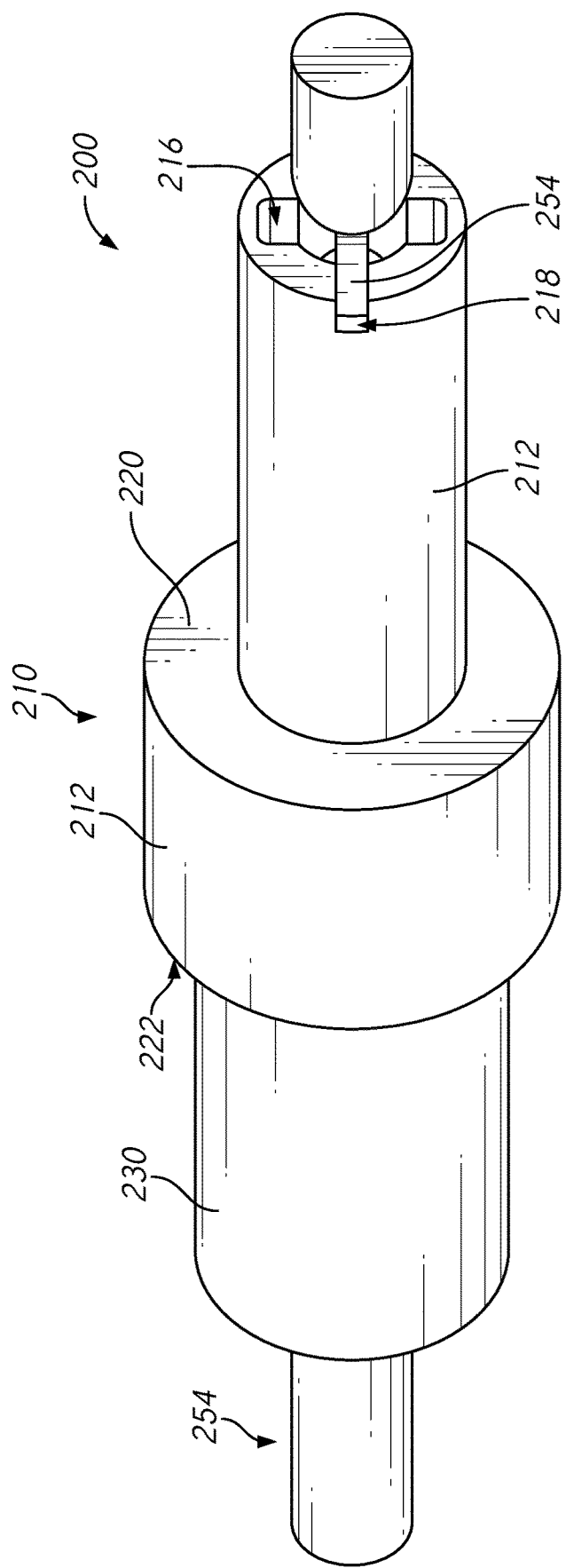
FIG. 5E is a schematic illustration of a nose being positioned over the elongated shaft in accordance with one or more embodiments of the present technology.

FIG. 5E illustrates the nose 230 being coupled with the elongated shaft 250 after the elongated shaft 250 is interlocked with the bumper 210. The nose 230 can be slid over the elongated shaft 250 until the proximal portion of the nose 230 contacts the distal face 222 of the bumper 210. Once the nose 230 contacts the bumper 210, the nose 230 can be coupled to the elongated shaft 250 by welding, soldering, or otherwise joining the nose 230 and the elongated shaft 250 together. By coupling the nose 230 with the elongated shaft 250, the elongated shaft 250 is prevented from moving proximally relative to the joining element 200, as the contact between the nose 230 and the bumper 210 would impede the elongated shaft 250 and prevent the elongated shaft 250 from moving proximally independent of the joining element 200. In some embodiments, the nose 230 can be coupled to the bumper 210 by welding, soldering, and/or otherwise joining the nose 230 with the bumper 210. By coupling the nose 230 to the bumper 210 and the elongated shaft 250, the elongated shaft 250 can be prevented from rotating independently of the joining element 200.

A method of coupling the elongated shaft 250 with the joining element 200 within a core member 102 will now be described. First, the bumper 210 is coupled to core member 102. The bumper 210 is coupled to the core member 102 by welding, soldering, and/or otherwise joining the bumper 210 to the tube 114. For example, the distal end portion of the tube 114 can be welded to the proximal face 220 of the bumper 210 and/or to the proximal portion 212, coupling the bumper 210 with the tube 114. After the bumper 210 is welded to the tube 114, the elongated shaft 250 is inserted into the aperture 216 of the bumper 210 through the distal face 222 of the bumper 210. In some embodiments, inserting the elongated shaft 250 into the aperture 216 can include aligning the radial direction R1 of the elongated shaft 250 with the A1 axis of the aperture 216. With the elongated shaft 250 positioned within the aperture 216, the elongated shaft 250 is then distally moved through the aperture 216 until the widened region 254 is through aperture 216, proximal to the proximal end of the proximal portion 212 and is free to rotate. Next, the elongated shaft 250 can be rotated so the widened region 254 aligns with the slot 218. Once the widened region 254 aligns with the slot 218, the elongated shaft 250 is moved distally until the widened region 254 is received within the slot 218, interlocking the elongated shaft with the proximal portion 212. Next, the nose 230 is slid over the elongated shaft 250 and positioned adjacent the bumper 210 so that the proximal face of the nose 230 contacts the distal face 222 of the bumper 210.

With the nose 230 contacting the bumper 210, the nose 230 is coupled to the elongated shaft 250 and the bumper 210. For example, the nose 230 can be soldered to the elongated shaft 250 and the bumper 210. Coupling the nose 230 with the elongated shaft 250 and bumper 210 along with positioning the widened region 254 within the slot 218 interlocks the elongated shaft 250 with the joining element 200. In some embodiments, the bumper 210 is welded to the tube 114 after the widened region 254 is positioned within the slot 218. In various embodiments, the elongated shaft 250 is initially moved through the proximal portion 212 of the joining element instead of the distal face 222 of the bumper 210.

Operating the system 100 to move the stent 105 will now be described. The stent 105 can be moved distally or proximally within the catheter 101 via the core member 102 and the stent coupling assembly 120. To move the stent 105 out of the catheter 101, the core member 102 is moved distally while the catheter 101 is held stationary, the core member 102 is held stationary while the catheter 101 is withdrawn proximally, or the core member 102 is moved distally while the catheter 101 is simultaneously withdrawn proximally. When the core member 102 is moved distally, the joining element 200 bears against the proximal end or edge of the stent 105 and causes the stent 105 to be advanced distally, and ultimately out of the of the catheter 101. In embodiments in which the engagement members 123 are employed to transmit pushing force to the stent 105, the mechanical engagement or interlock between the engagement members 123 and the stent 105, in response to the application of a distally directed force to the core member 102, causes the stent 105 to move distally through and out of the catheter 101. Conversely, to resheath or otherwise move the stent 105 into the catheter 101, the relative movement between the core member 102 and the catheter 101 is reversed compared to moving the stent 105 out of the catheter 101 such that the proximal region of the restraint 121 bears against the distal region of the spacer 125 and thereby causes the spacer 125, the release members 124, and the engagement members 123 to be retracted into the lumen 111 of the catheter 101. The mechanical engagement between the engagement members 123 and the stent 105 while the engagement members 123 are positioned within the lumen 111 holds the stent 105 with respect to the core member 102 such that proximal movement of the stent 105 relative to the catheter 101 enables re-sheathing of the stent 105 back into the catheter 101. This is useful when the stent 105 has been partially deployed and a portion of the stent 105 remains disposed between at least one of the engagement members 123 (e.g. the first engagement member 123a) and the inner surface of the catheter 101 because the stent 105 can be withdrawn back into the catheter 101 by moving the core member 102 proximally relative to the catheter 101 (and/or moving the catheter 101 distally relative to the core member 102). Resheathing in this manner remains possible until the engagement members 123 and/or catheter 101 have been moved to a point where the first engagement member 123a is beyond the distal opening of the catheter 101 and the stent 105 is released from between the first engagement member 123a and the catheter 101.

Conclusion

Although many of the embodiments are described with respect to devices, systems, and methods for delivery of stents, tubular implants such as filters, shunts or stent-grafts and other medical devices, other applications and other embodiments in addition to those described herein are within the scope of the present technology, and can be employed in any of the embodiments of systems disclosed herein, in place of a stent as is typically disclosed. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-5E.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A medical device delivery system comprising:
an elongated tubular member having a distal end portion, a proximal end portion, and a lumen extending therethrough;
a joining element coupled to a distal end portion of the elongated tubular member, the joining element comprising:
 a bumper having a distal end portion configured to engage a proximal portion of a medical device;
 a proximal portion adjacent the distal end portion of the elongated tubular member, wherein the proximal portion defines a slot having a length along a first direction; and
 an aperture extending through the bumper and the proximal portion of the joining element, the aperture having a first cross-sectional dimension along a second direction and a second cross-sectional dimension along a third direction different from the second direction, the first cross-sectional dimension being greater than the second cross-sectional dimension, wherein the first direction is about orthogonal to the second direction; and an elongated shaft having a distal region and a flattened region proximal of the distal region, the flattened region having a greatest cross-sectional dimension that is smaller than the first cross-sectional dimension of the aperture but larger than the second cross-sectional dimension of the aperture, wherein the flattened region is at least partially received within the slot.

2. The medical device delivery system of claim 1, wherein, when the flattened region is received within the slot, the flattened region prevents or limits distal movement of the elongated shaft with respect to the joining element.

3. The medical device delivery system of claim 1, the joining element further comprising a nose positioned over the elongated shaft and distal of the bumper.

4. The medical device delivery system of claim 3, wherein the nose is coupled to the elongated shaft.

5. The medical device delivery system of claim 1, wherein the elongated shaft is at least one of a wire, hypotube, or coil.

6. A medical device delivery system comprising:
   an elongated tubular member having a distal end portion, a proximal end portion, and a lumen extending therethrough;
   a joining element coupled to the distal end portion of the tubular member, the joining element comprising:
      a bumper having a proximal face abutting the distal end portion of the elongated tubular member;
      a proximal portion extending proximal of the proximal face and into the lumen of the elongated tubular member; and
      an aperture extending through the bumper and the proximal portion of the joining element, the aperture having a first cross-sectional dimension along a first radial axis and a second cross-sectional dimension along a second radial axis, the first cross-sectional dimension being greater than the second cross-sectional dimension; and
   an elongated shaft coupled to the joining element, the elongated shaft comprising:
      an intermediate portion extending distal to the bumper and configured to receive a medical device thereover;
      a proximal portion extending through the joining element aperture; and
      an engagement feature disposed along the proximal portion of the joining element, the engagement feature having a first radially outermost dimension along a first radial direction and a second radially outermost dimension along a second radial direction, the first radially outermost dimension being smaller than both the first cross-sectional dimension and the second-cross sectional dimension of the aperture, the second radially outermost dimension being smaller than the first cross-sectional dimension of the aperture but larger than the second cross-sectional dimension of the aperture.

7. The medical device delivery system of claim 6, wherein the proximal portion of the joining element comprises a slot configured to receive the engagement feature.

8. The medical device delivery system of claim 6, wherein the elongated shaft is substantially cylindrical, and wherein the engagement feature comprises a region of the elongated shaft that has been flattened.

9. The medical device delivery system of claim 6, wherein the first radial axis is substantially perpendicular to the second radial axis.

10. The medical device delivery system of claim 6, wherein a distal face of the bumper is configured to abut a proximal end of the medical device.

11. The medical device delivery system of claim 6, wherein the elongated tubular member is a hypotube having one or more flexibility-enhancing cuts along its length.

12. The medical device delivery system of claim 6, wherein the elongated shaft is a wire.

13. The medical device delivery system of claim 6, wherein the medical device is a stent.

14. The medical device delivery system of claim 6, wherein the medical device is a tubular braided implant.

15. A medical device delivery system comprising:
   a hypotube having a proximal portion, a distal portion, and a lumen extending therethrough;
   a joining element positioned at the distal portion of the hypotube, the joining element comprising:
      a bumper portion having a proximal-facing surface abutting a distal end of the hypotube;
      a proximal portion extending proximally from the distal portion such that the proximal portion is positioned within the lumen of the hypotube; and
      an aperture extending through the bumper portion and the proximal portion of the joining element, wherein the aperture has a first cross-sectional dimension along a first radial direction and a second cross-sectional dimension along a second radial direction, the second cross-sectional dimension being smaller than the first cross-sectional dimension; wherein the proximal portion of the joining element comprises a slot having a length along a third radial direction; and
   an elongated member having a proximally located attachment portion including a retention region extending through the aperture and a widened region extending laterally away from a longitudinal axis of the elongate member to a greater extent than the retention region, wherein the widened region is configured to fit through the aperture in a first orientation and to collide with the bumper portion and the proximal portion of the joining element in a second orientation.

16. The medical device delivery system of claim 15, wherein a distal face of the bumper portion is configured to abut a proximal end of a medical device.

17. The medical device delivery system of claim 15, wherein the widened region engages the proximal portion of the joining element and limits distal movement of the elongated member relative to the joining element.

18. The medical device delivery system of claim 15, wherein the widened region is configured to be received within the slot.

19. The medical device delivery system of claim 15, wherein the first radial direction is substantially perpendicular to the third radial direction.

* * * * *

UNITED STATES PATENT AND TRADEMARK OFFICE
CERTIFICATE OF CORRECTION

| | | |
|---|---|---|
| PATENT NO. | : 11,944,558 B2 | Page 1 of 1 |
| APPLICATION NO. | : 17/444502 | |
| DATED | : April 2, 2024 | |
| INVENTOR(S) | : Deen et al. | |

It is certified that error appears in the above-identified patent and that said Letters Patent is hereby corrected as shown below:

On the Title Page

Item (57), in Column 2, under "Abstract", Line 15, after "dimension" insert -- . --.

Signed and Sealed this
Fourteenth Day of May, 2024

Katherine Kelly Vidal
*Director of the United States Patent and Trademark Office*